(12) United States Patent
Morosawa et al.

(10) Patent No.: US 8,790,741 B2
(45) Date of Patent: Jul. 29, 2014

(54) PRIMER COMPOSITION FOR METAL OXIDE CERAMICS

(75) Inventors: Yusuke Morosawa, Takahagi (JP);
Mikio Kimura, Joso (JP)

(73) Assignee: Tokuyama Dental Corporation,
Taito-ku, Tokyo (JP)

( * ) Notice: Subject to any disclaimer, the term of this patent is extended or adjusted under 35 U.S.C. 154(b) by 225 days.

(21) Appl. No.: 13/057,051

(22) PCT Filed: Jul. 16, 2009

(86) PCT No.: PCT/JP2009/062888
§ 371 (c)(1),
(2), (4) Date: Feb. 1, 2011

(87) PCT Pub. No.: WO2010/016373
PCT Pub. Date: Feb. 11, 2010

(65) Prior Publication Data
US 2011/0143015 A1    Jun. 16, 2011

(30) Foreign Application Priority Data
Aug. 4, 2008  (JP) .................................. 2008-200940

(51) Int. Cl.
*A61C 13/23* (2006.01)
*A61L 24/00* (2006.01)
*A61K 6/00* (2006.01)

(52) U.S. Cl.
USPC ......... 427/2.26; 427/2.29; 523/113; 523/118; 523/120; 433/180

(58) Field of Classification Search
USPC ................... 427/2.26, 2.29; 523/120; 106/35; 433/180
See application file for complete search history.

(56) References Cited

U.S. PATENT DOCUMENTS 5,260,476 A     11/1993  Ohno et al.
6,191,190 B1 *  2/2001   Blackwell et al. ............ 523/115
2003/0113691 A1 * 6/2003  Ben-Yaakov et al. ......... 433/220
2009/0076189 A1 * 3/2009  Matsushige et al. .......... 523/120
2009/0093563 A1 * 4/2009  Qian ............................... 522/79

FOREIGN PATENT DOCUMENTS

| JP | 63-51308 A | 3/1988 |
| JP | 7-277913 A | 10/1995 |
| JP | 2000-248201 A | 9/2000 |
| JP | 2006-45179 A | 2/2006 |
| JP | 2007-238498 A | 9/2007 |
| JP | 2007238498 A * | 9/2007 |
| JP | 2009-114070 A | 5/2009 |
| WO | WO 2007/139207 A1 | 12/2007 |
| WO | WO 2007139207 A1 * | 12/2007 |

OTHER PUBLICATIONS

Machine Translation for JP 2007-238498 retreived Jun. 12, 2013.*
Extended Search Report from European Patent Office issued in corresponding European Patent Application No. 09804860.6 dated Jun. 22, 2011.
International Search Report (PCT/ISA/210) issued on Oct. 20, 2009, by Japanese Patent Office as the International Searching Authority for International Application No. PCT/JP2009/062888.
Kazuya Yamada et al., Effect of Single-liquid Priming Agents on Adhesive Bonding to Aluminum Oxide of a Methacrylic Resin, Dental Materials Journal 26(5), pp. 642-646, 2007.

* cited by examiner

*Primary Examiner* — Cachet Sellman
(74) *Attorney, Agent, or Firm* — Buchanan Ingersoll & Rooney PC

(57) ABSTRACT

A primer used for pre-treating the surfaces of a prosthetic, which exhibits a large adhering force at the time of adhering a prosthetic of metal oxide ceramics to an object to be joined by using an adhesive such as a dental cement, the large adhering force being maintained for extended periods of time even in a severe environment such as in an oral cavity. A primer composition for metal oxide ceramics includes (A) a polymerizable monomer component containing 5% by mass or more, preferably, 5% by mass to 80% by mass of an acidic group-containing polymerizable monomer as represented by a 11-methacryloyloxy-1,1-undecanedicarboxylic acid and a rest of a polymerizable monomer without acidic group, such as triethylene glycol dimethacrylate; (B) polyvalent metal ions resulting from a titanium tetrabutoxide or the like; and (C) an organic solvent such as acetone or ethyl alcohol, wherein water is not substantially contained.

8 Claims, No Drawings

PRIMER COMPOSITION FOR METAL OXIDE CERAMICS

TECHNICAL FIELD

This invention relates to a primer composition used for pre-treating the surfaces of metal oxide ceramics in order to improve adhering property.

BACKGROUND ART

A dental prosthetic of ceramics comprising chiefly silica has been used in the dental therapy in order to restore a decayed tooth or a broken tooth, or to restore a prosthetic.

The dental prosthetic of ceramics is, usually, joined to an object that is to be joined, such as tooth by using a dental cement such as resin-reinforced glass ionomer cement, resin ionomer cement or resin cement. These dental cements are all adhesives comprising chiefly a polymerizable monomer and a polymerization initiator, and require, in advance at the time of adhesion, the application of a primer (primer for ceramics) comprising chiefly a silane coupling agent onto the junction surfaces of the dental prosthetic of ceramics in order to enhance the adhering property. For instance, there have been proposed dental primers comprising, as a constituent component, an acidic organophosphorous compound having at least one radically polymerizable olefinic double bond in a molecule thereof (patent documents 1 and 2). In these dental primers, the acidic organophosphorous compound works as a catalyst for activating the silane coupling agent and for accelerating the condensation of silanol group on the surfaces of the ceramics. There has, further, been proposed a dental primer containing an acidic group-containing polymerizable monomer, polyvalent metal ions and a volatile organic solvent. However, this primer is applied to a cured body of resin and must contain water (patent document 3).

As the dental ceramics, on the other hand, there have been widely used metal oxide ceramics such as zirconia or alumina serving as dental prosthetic materials of all-ceramics featuring a larger strength. Even if treated with a general primer for ceramics comprising chiefly the silane coupling agent, however, these metal oxide ceramic materials are not capable of maintaining a sufficiently large adhering property for extended periods of time in a sever environment in an oral cavity. The reasons are attributed as described below. The dental ceramic material that is generally used chiefly comprises silica as described above and has many silanol groups on the surfaces thereof exhibiting favorable reactivity with the silane coupling agent. On the other hand, the metal oxide ceramics such as zirconia or alumina has almost no silanol group or only very few silanol groups, and does not react with the silane coupling agent. Therefore, it has been strongly desired to develop a primer for pre-treating the surfaces of metal oxide ceramics, having a new action and mechanism that meet properties of the metal oxide material in order to improve the adhering property.

As the primer for metal oxide ceramics, there has been proposed a dental adhesive composition containing a phosphonic acidic group-containing (meth)acrylate type monomer (patent document 4). There has been disclosed that the composition may contain a coupling agent in addition to the phosphonic acidic group-containing (meth)acrylate type monomer. Concretely, there have been disclosed titanate type coupling agents such as isopropyltriisostearoyl titanate, isopropyldimethacryloylisostearoyl titanate; and aluminum type coupling agents such as acetoalkoxyaluminum diisopropylate. There has, further, been proposed a primer for ceramics containing a (meth)acrylic acid ester type polymerizable monomer of a specific structure, such as 2-acetoacetoxyethyl methacrylate (patent document 5). The present inventors have tested the above novel primers for metal oxide ceramics for their adhering forces and have discovered that though all of them exhibit large initial adhering forces, their durability of adhesion is not sufficient. In particular, their adhering property decreases after the use in a severe environment in an oral cavity.

PRIOR ART DOCUMENTS

Patent Documents

Patent document 1: JP-A-63-51308
Patent document 2: JP-A-07-277913
Patent document 3: JP-A-2009-114070
Patent document 4: JP-A-2006-045179
Patent document 5: JP-A-2007-238498

Therefore, it has been strongly desired to develop a primer that can be used for pre-treating the surfaces of a prosthetic to exhibit a large adhering force when a prosthetic comprising metal oxide ceramics is adhered to an object to be joined by using an adhesive material such as dental cement, the large adhering force being maintained for extended periods of time even in a severe environment such as in an oral cavity.

BRIEF SUMMARY OF THE INVENTION

In order to overcome the above problems, the present inventors have forwarded a keen study paying attention to the adhering property on an interface between the metal oxide ceramics and the adhesive material, and have discovered that the adhering property on the interface improves if the surfaces of the ceramics are pre-treated with a liquid composition that contains an acidic group-containing polymerizable monomer, polyvalent metal ions and an organic solvent and, as a result, the adhering strength is improved between the object ceramics and the material to be joined, and that the above actions are affected by the presence of water and have, thus, completed the invention.

According to the present invention, there is provided a primer composition for metal oxide ceramics, comprising:
(A) a polymerizable monomer containing not less than 5% by mass of an acidic group-containing polymerizable monomer;
(B) polyvalent metal ions; and
(C) an organic solvent;
wherein water is not substantially contained.

In the above primer composition, it is desired that:
(1) the content of the polyvalent metal ions (B) is 0.001 to 6.00 meq per gram of the polymerizable monomer component (A);
(2) the organic solvent (C) is contained in an amount of 200 to 1750 parts by mass per 100 parts by mass of the polymerizable monomer component (A);
(3) the polyvalent metal ions (B) are metal ions resulting from a polyvalent metal compound; and
(4) a polymerization initiator (D) is, further, contained.

According to the present invention, there is, further, provided a dental primer composition comprising the above primer composition for metal oxide ceramics.

According to the present invention, further, there is provided a dental adhesion kit for prosthetics of metal oxide ceramics, comprising the above dental primer composition and a dental cement.

According to the present invention, further, there is provided a method of treating the surfaces of prosthetics by applying the above dental primer composition onto the surface of a dental prosthetic of metal oxide ceramics and, thereafter, removing the organic solvent by blowing the air.

The primer composition of the invention is applied onto the surface of the metal oxide ceramics and is, next, adhered to an object to be joined by using an adhesive material comprising chiefly a polymerizable monomer and a polymerization initiator to obtain a greatly improved adhering force and very excellent durability of adhesion in a severe environment. Therefore, the primer of the present invention can be preferably used when a dental prosthetic comprising metal oxide ceramics is to be joined to a tooth or other prosthetic by using a dental cement, and serves as a primer for pre-treating the surfaces, which is useful in the dental field. In this case, the two are joined together maintaining a large strength, and a large adhering force lasts for extended periods of time even in an environment in an oral cavity.

DETAILED DESCRIPTION OF THE INVENTION

The primer composition of the invention contains, as basic components, (A) a polymerizable monomer, (B) polyvalent metal ions and (C) an organic solvent and, further as required, (D) a polymerization initiator. These components will now be described in detail.

<(A) Polymerizable Monomers>

In the present invention, the polymerizable monomer (A) is a component used for imparting property of adhering to the metal oxide ceramics to the adhesive material such as dental cement. It is essential that not less than 5% by mass of the polymerizable monomer (A) is an acidic group-containing polymerizable monomer (A1) from the standpoint of improving the adhering property of the adhesive material to the metal oxide ceramics by improving the reactivity of an ionically crosslinked body that will be described later to the surfaces of the metal oxide ceramics and, further, by improving the penetrability (affinity) of the adhesive material into the primer component (adhesive layer) that contains the ionically crosslinked body. If the amount of the acidic group-containing polymerizable monomer (A1) is less than 5% by mass, the ionically crosslinked body that is formed exhibits a low reactivity to the surfaces of the metal oxide ceramics and, besides, the adhesive material penetrates less into the adhesive layer making it difficult to firmly join the metal oxide ceramics to the object that is to be joined. The polymerizable monomer (A) may all be the acidic group-containing polymerizable monomer (A1), but is desirably, further, blended with a polymerizable monomer without acidic group (A2) to adjust the strength of the adhesive interface and the penetrability of the adhesive material into the adhesive layer in order to obtain more excellent adhering property and durability of adhesion.

If described in detail, it is desired that the content of the acidic group-containing polymerizable monomer (A1) in the polymerizable monomer (A) is in a range of 5 to 80% by mass and, particularly, 20 to 70% because of the following reasons, and the rest is the polymerizable monomer (A2) without acidic group. The smaller the amount of the acidic group-containing polymerizable monomer (A1), the lower the reactivity of the formed ionically crosslinked body to the metal oxide ceramics and the lower the penetrability of the adhesive material into the primer component (adhesive layer) containing the ionically crosslinked body, making it difficult to maintain firm and long-lasting junction of the metal oxide ceramics and the object to be joined. The larger the above amount, the strength of the primer composition itself decreases and the adhering property decreases.

(A1) Acidic Group-Containing Polymerizable Monomer:

In the present invention, there is no particular limitation on the acidic group-containing polymerizable monomer provided it is a compound having at least one acidic group and at least one polymerizable unsaturated group in a molecule thereof, and any known compound can be used.

Described below are examples of the acidic group which the acidic group-containing polymerizable monomer has in a molecule thereof.

Examples of the Acidic Group:

[Chemical 1]

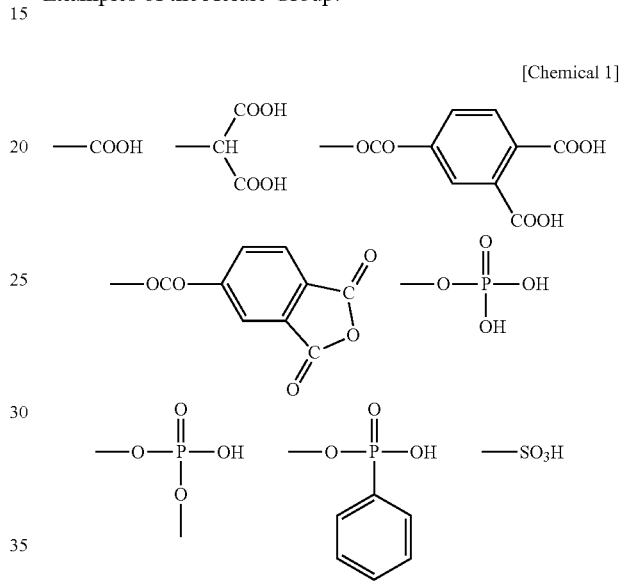

As the polymerizable unsaturated group which the acidic group-containing polymerizable monomer has in a molecule thereof, there can be exemplified acryloyl group, methacryloyl group, acrylamide group, methacrylamide group, vinyl group, allyl group, ethenyl group and styryl group. From the standpoint of curing rate, however, it is desired that the polymerizable unsaturated group is acryloyl group, methacryloyl group, acrylamide group or methacrylamide group.

In the present invention, the following compounds are representative examples of the acidic group-containing polymerizable monomer (A1) which has the acidic group and the polymerizable unsaturated group in a molecule thereof.

(A1) Acidic Group-Containing Polymerizable Monomers:

[Chemical 2]

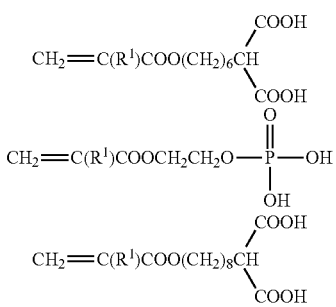

-continued $CH_2=C(R^1)COO(CH_2)_8O-P(=O)(OH)_2$ $CH_2=C(R^1)COO(CH_2)_{10}CH(COOH)_2$ $CH_2=C(R^1)COO(CH_2)_{10}O-P(=O)(OH)_2$ $CH_2=C(R^1)COO(CH_2)_{12}CH(COOH)_2$ $CH_2=C(R^1)COO(CH_2)_{12}O-P(=O)(OH)_2$ $CH_2=C(R^1)COO(CH_2)_{14}CH(COOH)_2$ $CH_2=C(R^1)COO(CH_2)_{14}O-P(=O)(OH)_2$ $CH_2=C(R^1)COO(CH_2)_{16}CH(COOH)_2$ $CH_2=C(R^1)COO(CH_2)_{16}O-P(=O)(OH)_2$ $CH_2=C(R^1)COO(CH_2)_{18}CH(COOH)_2$ $CH_2=C(R^1)COO(CH_2)_{18}O-P(=O)(OH)_2$ $CH_2=C(R^1)COO(CH_2)_{20}CH(COOH)_2$ $CH_2=C(R^1)COO(CH_2)_{20}O-P(=O)(OH)_2$

[Chemical 3]

$CH_2=C(R^1)COOCH_2CH_2OCO$-(phthalic anhydride)

$CH_2=C(R^1)COOCH_2CH_2O-P(=O)(OH)(OPh)$

-continued $CH_2=C(R^1)COO(CH_2)_8OCO$-(phthalic anhydride)

$CH_2=C(R^1)COO(CH_2)_8-P(=O)(OH)(OPh)$ $CH_2=C(R^1)COO(CH_2)_{10}OCO$-(phthalic anhydride)

$CH_2=C(R^1)COO(CH_2)_{10}-P(=O)(OH)(OPh)$ $CH_2=C(R^1)COO(CH_2)_{12}OCO$-(phthalic anhydride)

$CH_2=C(R^1)COO(CH_2)_{12}-P(=O)(OH)(OPh)$ $CH_2=C(R^1)COO(CH_2)_{16}O-P(=O)(OH)(OPh)$ $CH_2=C(R^1)COOCH_2CH_2OCO$-(benzene-1,2,4-tricarboxylic, 2,4-diCOOH)

$CH_2=C(R^1)COO(CH_2)_{20}O-P(=O)(OH)(OPh)$ $CH_2=C(R^1)COO(CH_2)_8OCO$-(benzene-1,2,4-tricarboxylic, 2,4-diCOOH)

$CH_2=C(R^1)COO(CH_2)_{12}OCO$-(benzene-1,2,4-tricarboxylic, 2,4-diCOOH)

[Chemical 4]

$CH_2=C(R^1)COOCH_2CH_2O-P(=O)(OH)-OCH_2CH_2OCOC(R^1)=CH_2$ $CH_2=C(R^1)COO(CH_2)_8O-P(=O)(OH)-O(CH_2)_8OCOC(R^1)=CH_2$ $CH_2=C(R^1)COO(CH_2)_{10}O-P(=O)(OH)-O(CH_2)_{10}OCOC(R^1)=CH_2$ $CH_2=C(R^1)COO(CH_2)_{12}O-P(=O)(OH)-O(CH_2)_{12}OCOC(R^1)=CH_2$

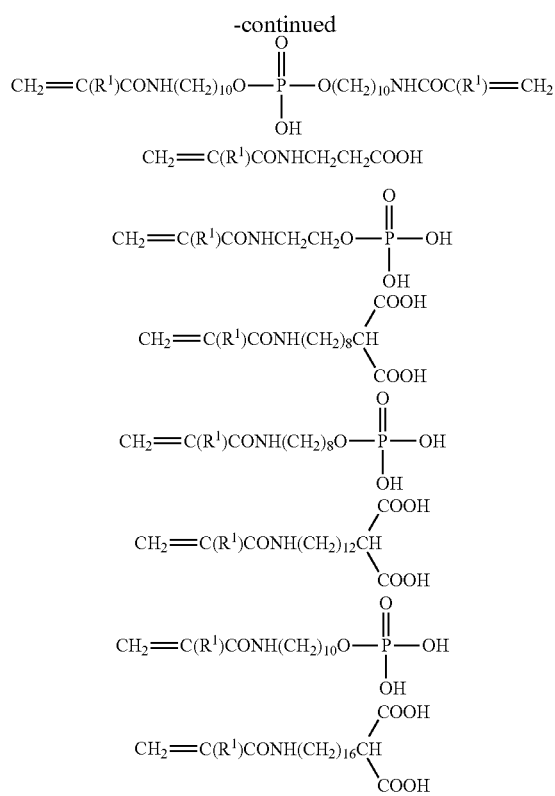

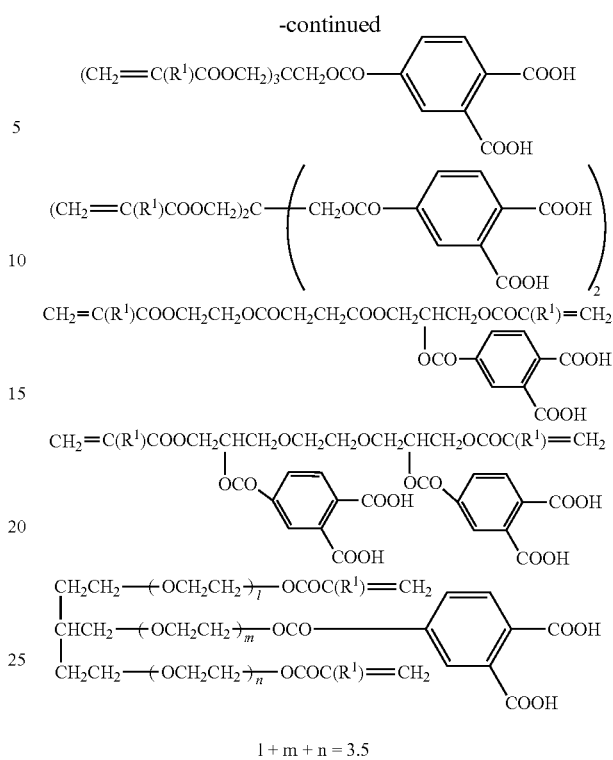

[Chemical 5]

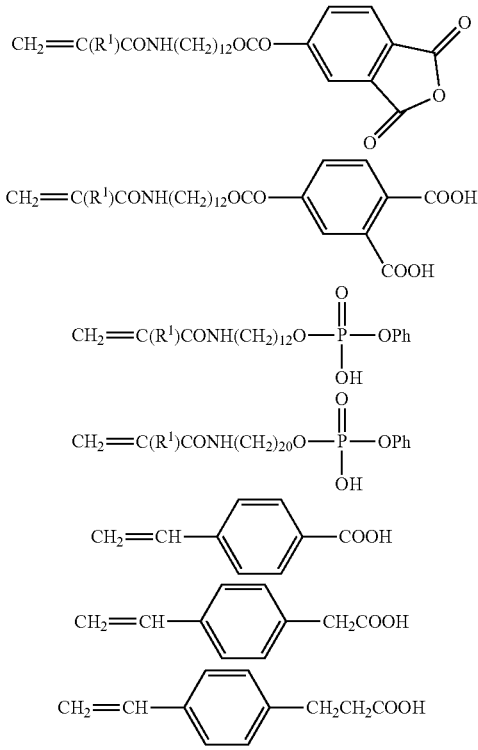

[Chemical 6]

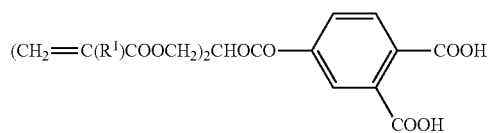

In the above compounds, $R^1$ is a hydrogen atom or a methyl group. As the acidic group-containing polymerizable monomers other than the above monomers, there can be exemplified vinylphosphonic acids in which a phosphoric acid group is directly bonded to a vinyl group, as well as acrylic acid, methacrylic acid and vinylsulfonic acid.

As the acidic group-containing polymerizable monomer, there is particularly preferably used an acidic group-containing polymerizable monomer in which an acidic group is bonded to a polymerizable unsaturated group via an aliphatic hydrocarbon group of a long chain having 6 to 20 carbon atoms because of its high hydrophobic property permitting little water to infiltrate into the adhesive interface and exhibiting improved durability of adhesion. The aliphatic hydrocarbon group present between the polymerizable unsaturated group and the acidic group has a length of chain of 6 to 20 carbon atoms and, preferably, 8 to 12 carbon atoms. Here, the length of chain of the aliphatic hydrocarbon group is the number of carbon atoms of the chain portion linking the polymerizable unsaturated group to the acidic group in the aliphatic hydrocarbon group, but does not include the number of carbon atoms of side chains that are possessed by the aliphatic hydrocarbon group. The long-chain aliphatic hydrocarbon group may not be saturated but is, preferably, saturated from the standpoint of chemical stability. Further, the long-chain aliphatic hydrocarbon group may be either a straight chain or a branched chain. Particularly preferably, the long-chain aliphatic hydrocarbon group is a long-chain alkylene group having the number of carbon atoms as described above since it can be synthesized relatively easily. As such an alkylene group, there can be exemplified hexylene group, heptylene group, octylene group, nonylene group, decylene group, undecylene group, dodecylene group, tetradecylene group, hexadecylene group and octadecylene group.

As the acidic group-containing polymerizable monomer having the above hydrophobic group, there can be exemplified the following polymerizable monomers, i.e.,
7-methacryloyloxy-1,1-heptanedicarboxylic acid,
9-methacryloyloxy-1,1-nonanedicarboxylic acid,
11-methacryloyloxy-1,1-undecanedicarboxylic acid,
13-methacryloyloxy-1,1-tridecanedicarboxylic acid,
15-methacryloyloxy-1,1-pentadecanedicarboxylic acid,
17-methacryloyloxy-1,1-heptadecanedicarboxylic acid,
18-methacryloyloxy-1,1-octadecanedicarboxylic acid,
6-methacryloyloxyhexyldihydrogene phosphate,
8-methacryloyloxyoctyldihydrogene phosphate,
10-methacryloyloxydecyldihydrogene phosphate,
12-methacryloyloxydodecyldihydrogene phosphate,
14-methacryloyloxytetradecyldihydrogene phosphate,
16-methacryloyloxyhexadecyldihydrogene phosphate,
18-methacryloyloxyoctadecyldihydrogene phosphate, and
20-methacryloyloxyicocyldihydrogene phosphate.

The acidic group-containing polymerizable monomers can be used in a single kind or being mixed in two or more kinds together. Use of the monomer having, in a molecule thereof, two or more groups [—OH] capable of being ionically bonded to polyvalent metal ions that will be described later, is desired from the standpoint of improving the strength by ionic bond.

(A2) Polymerizable Monomers without Acidic Group:

There is no particular limitation on the polymerizable monomer (A2) without acidic group used for the polymerizable monomer (A) of the invention provided it is a compound that has no acidic group but has at least one polymerizable unsaturated group in a molecule thereof, and any known compound can be used. As the polymerizable unsaturated groups, there can be exemplified those described above concerning the acidic group-containing polymerizable monomer (A1) and, particularly desirably, acryloyl group, methacryloyl group, acrylamide group and methacrylamide group.

As the polymerizable monomer without acidic group, there can be concretely exemplified mono(meth)acrylate type monomers such as methyl (meth)acrylate {meaning methyl acrylate or methyl methacrylate, hereinafter the same}, ethyl (meth)acrylate, pentyl (meth)acrylate, hexyl (meth)acrylate, 2-(meth)acryloxyethylacetyl acetate, 2-(meth)acryloxyethyl acetate, 2-(meth)acryloxyethyl propionate and 3-(meth)acryloxypropyl acetate; and polyfunctional (meth)acrylate type monomers such as ethylene glycol di(meth)acrylate, diethylene glycol di(meth)acrylate, triethylene glycol di(meth)acrylate, propylene glycol di(meth)acrylate, dipropylene glycol di(meth)acrylate, 2,2'-bis[4-(meth)acryloyloxyethoxyphenyl]propane, 2,2'-bis[4-(meth)acryloyloxyethoxyethoyphenyl]propane, 2,2'-bis{4-[3-(meth)acryloyloxy-2-hydroxypropoxy]phenyl}propane, 1,4-butanediol di(meth)acrylate, 1,6-hexanediol di(meth)acrylate, trimethylolpropane tri(meth)acrylate, urethane(meth)acrylate, tetraethylene glycol di(meth)acrylate, pentaethylene glycol di(meth)acrylate and glyceryl di(meth)acrylate.

As the polymerizable monomer without acidic group other than the above (meth)acrylate type monomers, there can be exemplified fumaric acid ester compounds such as monomethyl fumarate, diethyl fumarate and diphenyl fumarate; styrene type compounds such as styrene, divinylbenzene, α-methylstyrene and α-methylstyrene dimer; allyl compounds such as diallyl phthalate, diallyl terephthalate, diallyl carbonate and allyl diglycol carbonate. The polymerizable monomers without acidic group can be used in a single kind or being mixed in two or more kinds together.

<(B) Polyvalent Metal Ions>

It is important that the primer composition of the present invention contains polyvalent metal ions (B). The polyvalent metal ions form an ionically crosslinked body with the acidic group-containing polymerizable monomer in the organic solvent (C). It is considered that upon applying the primer composition of the invention onto a member comprising metal oxide ceramics and drying the organic solvent, the ionically crosslinked body is condensed on the surfaces of the metal oxide ceramics and, particularly, on the base points on the surfaces. As a result, ionic crosslinking is, further, accelerated between the acidic group-containing polymerizable monomer and the polyvalent metal ions, and the reactivity to the metal oxide ceramics is, further, enhanced. Next, upon applying the adhesive material onto the primer-treated surface, the adhesive material penetrates into the primer component (adhesive layer) that contains the ionically crosslinked body. Thereafter, when the object to be joined is joined and the adhesive material is cured by polymerization, the crosslinking density increases in the cured body of the adhesive material on the adhesive interface due to synergetic effect of the curing by polymerization and the ionic crosslinking. As a result, it is presumed that the water-resisting property is improved and a high adhering property is maintained between the metal oxide ceramics and the object to be joined.

The polyvalent metal ions are metal ions having a valency of two or more that can be bonded to acidic groups possessed by the acidic group-containing polymerizable monomer, and any polyvalent metal ions can be used so far as they are capable of being bonded to acidic groups. Concrete examples include ions of magnesium, calcium, strontium, barium, zinc, copper (II) and tin (II) as divalent metal ions; ions of aluminum, gallium, indium, scandium, yttrium, lanthanum, cerium, praseodymium, promethium, neodymium, samarium, europium, gadolinium, terbium, dysprosium, holmium, erbium, thulium, ytterbium, iron (III) and actinium as trivalent metal ions; and ions of titanium, zirconium, vanadium, hafnium and tungsten (IV) as metal ions of a valency of four or more. Among them, ions having a valency of three or more are preferred from the standpoint of adhering property. In particular, aluminum ions, lanthanum ions and titanium ions are most desired from the standpoint of safety to the living body in addition to high adhering property.

In the present invention, the amount of polyvalent metal ions (meq) is the amount of ionic bond by polyvalent metal ions per gram of the polymerizable monomer component (A), which is expressed by milliequivalent (meq), and is the sum of values obtained by multiplying ion concentrations (mmols/g) contained in a gram of the polymerizable monomer component (A) by their respective valencies. The ionic concentrations can be measured by the ICP (inductively coupled plasma) emission spectroscopy.

It is desired that the primer composition of the present invention contains the polyvalent metal ions (B) in an amount of 0.001 meq to 6.00 meq per gram of the polymerizable monomer component (A) from the standpoint of adhering property. In order to obtain the strength of the adhesive interface and adjust the penetrability of the adhesive material such as dental cement into the primer composition to obtain more excellent adhering property and durability of adhesion, further, it is desired that the polyvalent metal ions (B) are present in an amount of 0.001 to 3.00 meq and, more preferably, 0.01 to 2.00 meq per gram of the polymerizable monomer component (A). With the amount of the polyvalent metal ions lying in this range, it is made possible to form a strong adhesive layer which is based on a suitable degree of ionic crosslinking in the interface between the metal oxide ceramics and the adhesive material, and the adhesive material penetrates more into the adhesive layer. If the amount of the polyvalent metal ions is less than 0.001 meq, the ionic crosslinking becomes insufficient and the adhering property tends to become insufficient. If the amount thereof is not smaller than 6.00 meq, the adhesive material penetrates less into the adhesive layer and the adhering property tends to decrease.

It is, further, desired that the total ionic valency of the polyvalent metal ions (B) in the primer composition is 0.001 to 2.00 and, more preferably, 0.01 to 1.00 to the total valency of acids of the acidic group-containing polymerizable monomer (A1) contained in the polymerizable monomer component (A) from the standpoint of obtaining favorable adhering property. Most desirably, the total ionic valency of the polyvalent metal ions (B) is 0.01 to 0.8 to the total valency of acids of the acidic group-containing polymerizable monomer (A1) from the standpoint of obtaining particularly favorable adhering property by permitting part of acidic groups of the acidic group-containing polymerizable monomer (A1) to remain and enabling the ionically crosslinked body to easily act on the base points on the surfaces of the metal oxide ceramics. The total valency of the polyvalent metal ions is the one obtained by multiplying a mol number of the polyvalent metal ions contained in the primer composition by the valency of the polyvalent metal ions. For example, if the polyvalent metal ions are titanium ions, the valency is 4. Further, if the polyvalent metal ions consist of a mixture of ions having a valency of 3 and ions having a valency of 4, the total valencies of ions are found for the respective kinds of metal ions and are added up. On the other hand, the total valency of acids of the acidic group-containing polymerizable monomer is a value obtained by multiplying a mol number of the acidic group-containing polymerizable monomer contained in the primer composition by a valency of acids in the acidic group-containing polymerizable monomer. For example, if the acidic group-containing polymerizable monomer is 11-methacryloyloxy-1,1-undecanedicarboxylic acid, the valency of acid is 2. Further, if the acidic group-containing polymerizable monomer is a mixture of the one having an acid valency of 2 and the one having an acid valency of 1, the total valencies of acids are found for the respective kinds of the acidic group-containing polymerizable monomers and are added up. In the primer composition of the present invention, therefore, the ratio of "the total valency of the polyvalent metal ions"/"the total valency of acids of the acidic group-containing polymerizable monomer" is, preferably, 0.001 to 2.00, more preferably, 0.01 to 1.00 and, further preferably, 0.01 to 0.8 from the standpoint of adhering strength.

In the present invention, there is no particular limitation on the method of making polyvalent metal ions present in the primer composition. Namely, in preparing the primer composition, a material that serves as a source of polyvalent metal ions may be added or contacted to the composition that contains the polymerizable monomer component (A) and the organic solvent (C) so that the polyvalent metal ions are released in the above-mentioned amount into the composition. As the source of polyvalent metal ions, a simple metal may be used. Usually, however, a polyvalent metal compound that can be easily ionized is favorably used.

(B1) Polyvalent Metal Compounds:

As the polyvalent metal compound, it is desired to use a metal salt of an acid having a pKa value, at least, higher than the pKa value which is based on the first dissociation of an acidic group of the acidic group-containing polymerizable monomer, i.e., to use a metal salt of an acid weaker than the acidic group-containing polymerizable monomer. If there is used a salt of an acid stronger than the acidic group-containing polymerizable monomer, the ionic bond does not take place to a sufficient degree between the free polyvalent metal ions and the acidic groups of the acidic group-containing polymerizable monomer, which is not desirable.

As the polyvalent metal salt of an acid weaker than the acidic group-containing polymerizable monomer, there can be exemplified carbonate, enolate of 1,3-diketone, citrate, tartarate, halide, malonate, glycolate, lactate, phthalate, isophthalate, terephthalate, acetate and methoxyacetate. Among the polyvalent metal salts of these weak acids, some may have very low solubility depending upon the kinds of polyvalent metals. Therefore, they should be used after having confirmed the solubility by conducting experiments in advance. As the polyvalent metal compounds, further, there can be also used hydroxide, hydride and alkoxide. Among these polyvalent metal compounds, it is desired to use carbonate, hydroxide, hydride or fluoride of a polyvalent metal, or a lower alkoxide thereof having not more than 4 carbon atoms from such a standpoint that the polyvalent metal ions quickly elute out and that the by-product thereof is a gas at normal temperature, water or lower alcohol that does not affect the adhering property and that can be easily removed. From the standpoint of easy handling, it is more desired to use hydroxide, fluoride or alkoxide of a polyvalent metal.

Here, as the polyvalent metal compound (B1), it is not allowed to use titanate type coupling agents such as isopropyltriisostearoyl titanate, isopropyldimethacryloylisostearoyl titanate; and aluminum type coupling agents such as acetoalkoxyaluminum diisopropylate. This is because the above coupling agents all have groups that cannot be hydrolyzed being bonded to the center metals. Therefore, even if these coupling agents were mixed with the acidic group-containing polymerizable monomer, the polyvalent metal ions (B) which are the basic components of the invention are not eluted out.

Preferred concrete examples of the polyvalent metal compound include, as divalent metal ion sources, calcium carbonate, calcium hydroxide, calcium ethoxide, strontium carbonate, strontium hydroxide, strontium ethoxide, barium carbonate, barium hydroxide, barium isopropoxide, zinc carbonate, zinc hydroxide, zinc ethoxide, zinc ethoxymethoxide, copper (II) methoxide and tin (II) methoxide. As the trivalent metal ion sources, there can be exemplified aluminum methoxide, aluminum ethoxide, aluminum isopropoxide, aluminum butoxide, aluminum hydroxide, aluminum acetylacetonato, aluminum fluoride, gallium ethoxide, indium ethoxide, scandium isopropoxide, yttrium isopropoxide, lanthanum methoxide, lanthanum ethoxide, lanthanum isopropoxide, lanthanum butoxide, lanthanum hydroxide, lanthanum carbonate, lanthanum fluoride, cerium isopropoxide, praseodymium isopropoxide, promethium isopropoxide, neodymium isopropoxide, samarium isopropoxide, europium isopropoxide, gadolinium isopropoxide, terbium ethoxide, terbium methoxide, dysprosium isopropoxide, holmium isopropoxide, erbium isopropoxide, thulium isopropoxide, ytterbium isopropoxide, iron (III) ethoxide and actinium ethoxide. As the metal ion sources having a valency of four or more, there can be exemplified titanium methoxide, titanium ethoxide, titanium isopropoxide, titanium butoxide, titanium hydroxide, titanium fluoride, zirconium ethoxide, zirconium isopropoxide, zirconium butoxide, tungsten (IV) methoxide, tungsten (IV) isopropoxide and tungsten (IV) butoxide.

Among them, particularly preferred examples are aluminum methoxide, aluminum ethoxide, aluminum isopropoxide, aluminum butoxide, aluminum hydroxide, aluminum fluoride, lanthanum methoxide, lanthanum ethoxide, lanthanum isopropoxide, lanthanum butoxide, lanthanum hydroxide, lanthanum carbonate, lanthanum fluoride, titanium methoxide, titanium ethoxide, titanium isopropoxide, titanum butoxide, titanium hydroxide and titanium fluoride.

<(C) Organic Solvents>

In the present invention, the organic solvent (C) is used for homogeneously and stably dispersing the components. The organic solvent (C) is used in an amount in a range of 100 to 2000 parts by mass, preferably, 200 to 1750 parts by mass from the standpoint of adhering force and, more preferably, 200 to 1500 parts by mass per 100 parts by mass of the polymerizable monomer component (A). If the amount of the organic solvent (C) is less than 100 parts by mass, the primer composition remains in excess amounts on the adhering surface of the metal oxide ceramics, the water-resisting property decreases and satisfactory adhering property is not obtained. If the amount thereof exceeds 2000 parts by mass, on the other hand, the concentration of the component that contributes to the adhesion decreases in the primer composition, and the strength of adhesion tends to decrease.

In the primer composition of the present invention as described above, an ionically crosslinked body is formed between the polyvalent metal ions and the acidic groups of the acidic group-containing polymerizable monomer. If the reactivity thereof is high, however, gelation may take place during the storage in case the form of package during the storage is one-liquid form (one-package form). It may, further, become difficult to smoothly apply the primer composition onto the metal oxide ceramics. The organic solvent, on the other hand, enables the polyvalent metal ions to be suitably diluted and prevents gelation that stems from the ionically crosslinked body, solving the problem of storage stability.

As described above, the primer composition of the present invention is applied onto the surface of the metal oxide ceramics (surface on where the adhesive material is to be applied). Thereafter, the air is blown thereto to volatilize the organic solvent so that the ionically crosslinked body is condensed on the surface of the metal oxide ceramics. As a result, the ionic crosslinking is accelerated between the acidic group-containing polymerizable monomer and the polyvalent metal ions to enhance the adhering property between the surface of the metal oxide ceramics and the adhesive material. It is, therefore, desired that the organic solvent used in the present invention is volatile at room temperature.

Volatile referred to here stands for that the boiling point under 760 mmHg is not higher than 200° C. and that the vapor pressure at 20° C. is not lower than 0.5 KPa. Concrete examples of the organic solvent that can be favorably used in the present invention include alcohols such as methanol, ethanol, isopropyl alcohol and butanol; ketones such as acetone and methyl ethyl ketone; ethers such as ethyl ether, 1,4-dioxane and tetrahydrofuran; esters such as ethyl acetate and ethyl formate; aromatic solvents such as toluene, xylene and benzene; hydrocarbon type solvents such as pentane, hexane, heptane and octane; chlorine type solvents such as methylene chloride, chloroform and 1,2-dichloroethane; and fluorine type solvents such as trifluoroethanol, etc. As required, these organic solvents may be used in a plurality of kinds being mixed together. If toxicity to the living body is taken into consideration, it is particularly desired to use acetone, ethanol and isopropanol.

It is important that the primer composition of the present invention does not substantially contain water. Presence of water in the composition hinders the reaction of the ionically crosslinked body on the surface of the metal oxide ceramics and, particularly, at the base points resulting, therefore, in the deteriorated strength of adhesion and deteriorated sustenance thereof. Here, water is not substantially contained stands not only for that water is not arbitrarily contained as a component of the primer composition of this invention, as a matter of course, but also for that if the total amount of the primer composition of the invention is 100 parts by weight, then water is contained in an amount of less than 1 part by weight, preferably, less than 0.1 part by weight and, more preferably, less than 0.01 part by weight.

<(D) Polymerization Initiators>

To further improve the adhering property to the adhesive material, the primer composition of the present invention can be further blended with a polymerization initiator (D). As the polymerization initiator, there can be exemplified chemical polymerization initiators and photo polymerization initiators.

The chemical polymerization initiator stands for the one that comprises a plurality of components which when contacted to each other form polymerization initiating species (radicals). Concretely, there can be exemplified a system comprising an aryl borate compound and an acidic compound, a system comprising a sulfinic acid (or sulfinate) and an acidic compound, a system comprising an organic peroxide and an amine compound, a system comprising an azo compound and an organic peroxide, and a system comprising a pyrimidinetrione derivative, a halogen ion-forming compound and a metal ion-forming compound. Among them, the system comprising an aryl borate compound and an acidic compound, the system comprising a sulfinic acid (or a sulfinate) and an acidic compound, and the system comprising an organic peroxide and an amine compound are desired because of their high polymerizing activity and excellent safety to the ecology. The system comprising an aryl borate compound and an acidic compound, and the system comprising a sulfinic acid (or a sulfinate) and an acidic compound are more desired from such a reason that the composition containing the acidic group-containing polymerizable monomer has a high polymerizing activity. In the system comprising an aryl borate compound and an acidic compound, further, it is desired to also use, as a polymerization promotor, a metal compound having a valency +II, +III, +IV or +V which is a decomposition promotor for the organic peroxide and, preferably, a vanadium compound having a valency +IV and/or +V, and/or an organic peroxide which is an oxidizing agent. Here, the metal compound that can be added as the decomposition promotor is the one which does not substantially (almost) permit polyvalent metal ions (B) to be eluted out in the composition of the invention, and is distinguished from the polyvalent metal compound (B1) mentioned above.

As the aryl borate compound, there can be used any known compound without limitation. Particularly preferred examples include amine salts such as tetraphenylboron, tetra(p-fluorophenyl)boron, tetra(p-chlorophenyl)boron, trialkyl(p-fluorophenyl)boron, trialkyl(3,5-bistrifluoromethyl)phenylboron and dialkyldiphenylboron, and sodium salts.

As the sulfinic acids (or sulfinates), there can be used known ones without limitation. Particularly preferred examples include aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid or salts thereof such as sodium benzenesulfinate, lithium benzenesulfinate, sodium p-toluenesulfinate, lithium p-toluenesulfinate, potassium p-toluenesulfinate, sodium m-nitrobenzenesulfinate and sodium p-fluorobenzenesulfinate.

The acidic compound does not have to be separately added; i.e., the acidic group-containing polymerizable monomer (A1) contained in the primer composition of the present invention can be utilized. As will be obvious from the above preferred amount of the polyvalent metal ions, in the primer composition according to the embodiment of the invention, the acidic groups of the acidic group-containing polymerizable monomer may not often be all neutralized by the ionic crosslinking with the polyvalent metal ions. In this case, the "acidic" function can be provided by the remainder of acidic groups of the acidic group-containing polymerizable monomer. When the acidic groups of the acidic group-containing polymerizable monomer are almost all neutralized or when the amount of the acidic compound relying upon the remainder of the acidic groups is not sufficient, other acidic compounds may be added until a sufficient degree of acidity is exhibited. As other acidic compounds, there can be used any known inorganic acids or organic acids without particular limitation if an aqueous solution or an aqueous suspension in which they are dissolved or suspended exhibits acidity. Preferably, there can be used known acidic compounds such as nitric acid, sulfuric acid, hydrochloric acid, phosphoric acid and acetic acid within a range in which they do not impair the adhering property. If an acidic compound which is more strongly acidic than the acidic group-containing polymerizable monomer is added, however, the adhering property may be adversely affected as described above. It is, therefore, desired to use a weakly acidic compound.

As the metal compound having a valency +II, +III, +IV or +V used as a polymerization promotor in the system comprising the aryl borate compound and the acidic compound, there can be added a metal compound that does not correspond to the polyvalent metal compound (B1) described above. Namely, there can be used vanadium compound, iron compound, copper compound, molybdenum compound, manganese compound, cobalt compound, tungsten compound and tin compound. Among them, a vanadium compound having a valency +IV and/or +V is preferred. Concrete examples include such vanadium compounds as divanadium (IV) tetroxide, vanadium (IV) oxide acetylacetonato, vanadium (IV) oxobis(1-phenyl-1,3-butanedionate), oxovanadium (IV) bis(maltolato), vanadium (V) pentoxide, sodium (V) metavanadate, and ammon (V) metavanadate.

As the organic oxide which is also the polymerization promotor, there can be exemplified ketone peroxide, peroxyketal, hydroperoxide, diaryl peroxide, peroxy ester, diacyl peroxide and peroxydicarbonate. Among them, diacyl peroxides or hydroxyperoxides are particularly preferred. As the diacyl peroxides, there can be concretely exemplified isobutyl peroxide, 2,4-dichlorobenzoyl peroxide, 3,5,5-trimethylhexanoyl peroxide, octanoyl peroxide and lauroyl peroxide. As the hydroperoxides, there can be exemplified p-methane hydroperoxide, diisopropylbenzene peroxide, 1,1,3,3-tetramethylbutyl hydroperoxide and cumene hydroperoxide.

As the photo polymerization initiator, there can be exemplified a compound which forms radical species upon being decomposed by itself by the irradiation with light and a system thereof to which a polymerization promotor is added. As concrete compounds, there can be preferably used α-diketones such as camphorquinone, benzyl, α-naphthyl, acetonaphthene, naphthoquinone, 1,4-phenanthrenequinone, 3,4-phenanthrenequinone and 9,10-phenanthrenequinone; thioxanthones such as 2,4-diethylthioxanthone; α-aminoacetophenones such as 2-benzyl-dimethylamino-1-(4-morpholinophenyl)-butanone-1,2-benzyl-dimethylamino-1-(4-morpholinophenyl)-butanone-1,2-benzyl-dimethylamino-1-(4-morpholinophenyl)-propanone-1; and acylphosphinoxide derivatives such as 2,4,6-trimethylbenzoyldiphenyl phosphinoxide and bis(2,6-dimethoxybenzoyl)-2,4,4-trimethylpentyl phosphinoxide.

As the polymerization promotor, there can be exemplified tertiary amines such as N,N-dimethylaniline, N,N-dibenzylaniline, N,N-dimethyl-p-toluidine, N,N-diethyl-p-toluidine, m-chloro-N,N-dimethylaniline, p-dimethylaminobenzaldehyde, p-dimethylaminoacetophenone, p-dimethylaminobenzoic acid, ethyl p-dimethylaminobenzoate, amyl p-dimethylaminobenzoate, N,N-dihydroxyethylaniline, N,N-dihydroxyethyl-p-toluidine, p-dimethylaminostilbene, N,N-dimethyl-3,5-xylidine, N,N-dimethyl-β-naphthylamine, tributylamine, tripropylamine, triethylamine, N-methyldiethanolamine, N-ethyldiethanolamine, N,N-dimethylstearylamine and N,N-dimethylaminoethyl acrylate; barbituric acids such as 5-butylbarbituric acid and 1-benzyl-5-phenylbarbituric acid; and mercapto compounds such as dodecylmercaptane and pentaerythritoltetrakis(thioglycolate). Among them, α-diketones and acylphosphinoxide derivatives are most desired.

According to the invention, the amount of the polymerization initiator (D) [when the acidic group-containing polymerizable monomer serves as an acidic compound and, hence, works as a component of the polymerization initiator, the acidic group-containing polymerizable monomer is not included as the polymerization initiator] can be suitably set without any particular limitation if the amount is enough for curing the adhesive layer. Preferably, the amount of the polymerization initiator (D) is 0.01 to 10 parts by mass and, more preferably, 0.1 to 5 parts by mass per 100 parts by mass of the polymerizable monomer component (A). If the amount thereof is less than 0.01 part by mass, the polymerization tends to become insufficient. If the amount thereof exceeds 10 parts by mass, the strength of the cured polymer decreases, which is not desirable.

<Other Blending Agents>

To the primer composition of the present invention, there can be added an organic viscosity-imparting agent of a high molecular compound such as polyvinyl pyrrolidone, carboxymethyl cellulose or polyvinyl alcohol within a range in which they do not deteriorate the properties. As desired, further, there can be selectively used various additives such as filler, ultraviolet-ray absorber, dye, antistatic agent, pigment and perfume.

<Application of the Primer Composition>

The primer composition of the invention is, usually, stored in the form of one liquid in which various components are mixed, i.e., stored in a sealed container in the form of one package. At the time of use, the primer composition is taken out in a required amount from the container and is applied onto a predetermined region. Namely, at the time of use, there is no need of cumbersome operation for mixing the components together, reducing the labor and making it possible to stably maintain a predetermined strength of adhesion. Here, the primer composition stored in the one-package form may easily undergo gelation during the storage since the amount of the organic solvent is relatively small. In such a case, the basic components of the invention may be divided into two or more liquids and at the time of use, these components may be used being mixed together. For instance, the acidic group-containing polymerizable monomer component (A1) and the polyvalent metal ion component (B) may be stored in separate packages, and other components may be stored in a package that contains either (A1) or (B) or may be stored being mixed into both packages in amounts of a suitable ratio. At the time of use, the components are mixed together.

The primer composition of the present invention is used for improving the adhering property by treating the surfaces of the metal oxide ceramics, e.g., used for fixing a prosthetic of the metal oxide ceramics to a part of a tooth that is restored or for restoring the broken prosthetic that is fixed to a restored part of the tooth. To fix the prosthetic of the metal oxide ceramics to the restored part of the tooth, the surface of the prosthetic formed in a predetermined shape is suitably polished. Thereafter, a predetermined amount of the primer composition is applied thereon, and the organic solvent in the composition is removed by blowing the air thereto. Next, a paste of dental cement is applied onto the primer composition and is adhered to the restored part of the tooth. Thereafter, the resin cement is cured by chemical polymerization or photo polymerization. As a result, the prosthetic is adhered and fixed by the resin cement to the restored part of the tooth. Further, when the prosthetic itself that is broken is to be restored, the primer composition is applied in predetermined amounts onto the broken surfaces of the prosthetic that is broken and split off and of the prosthetic remaining on the tooth, and the organic solvent is removed by blowing the air thereto. Thereafter, in the same manner as described above, the paste of dental cement is applied onto the surface of either prosthetic to fix again the prosthetic that is broken and split off. Instead of the broken prosthetic, further, there can be used a prosthetic that is newly formed in the same shape. The new prosthetic is similarly adhered and fixed to the prosthetic remaining on the tooth.

It is desired that the primer composition taken out from the container or is obtained by being mixed together when it is stored in the form of two liquids, is operated as quickly as possible so as to be applied onto the prosthetic before the organic solvent volatilizes. If the organic solvent volatilizes and its amount decreases before the primer composition is applied onto the prosthetic, then improvement in the adhering property cannot be expected. It is, therefore, desired that the operation for application is conducted in about several minutes after it is taken out from the container.

<Metal Oxide Ceramics>

As the metal oxide ceramics to be pretreated, there can be exemplified compounds comprising oxygen which is contained in a state of having an oxidation number −2 and a metal element. There is no particular limitation on the metal element that constitutes the oxide and any metal element can be selected. The metal elements can be used in one kind or in a plurality of kinds. Preferred examples of the metal element include those of the Group 1, such as lithium, sodium and potassium; those of the Group 2, such as magnesium, calcium, strontium and barium; those of the Group 3, such as yttrium and lanthanum; those of the Group 4, such as titanium, zirconium and hafnium; and those of the Group 13, such as aluminum and indium. Among them, it is more preferred to use those which chiefly comprise metal elements of the Group 4, such as titanium, zirconium and hafnium, and of the group 13, such as aluminum and indium from the standpoint of less toxicity and high effect of the primer composition of the invention, and is most preferred to use zirconium and aluminum from the standpoint of a large strength of when an oxide is formed. Concrete examples of the metal oxide ceramics include those ceramics that comprise zirconium oxide and aluminum oxide. There is no limitation on the objects onto which the primer of the invention is to be applied provided they comprise the metal oxide ceramics. Most practical objects are restoring materials such as inlay, underlay, crown and the like.

<Adhesive Materials>

There is no particular limitation on the adhesive material for improving the adhering property to the metal oxide ceramics by using the primer composition of the invention, provided it is a polymerizable composition containing a polymerizable monomer and a polymerization initiator as chief components. There can be used any known polymerizable monomer without limitation, such as vinyl type polymerizable monomer, styrene type polymerizable monomer and allyl type polymerizable monomer. From the standpoint of large adhering property, however, a (meth)acrylic type polymerizable monomer is most desired. As the (meth)acrylic type polymerizable monomer to be used for the adhesive material, there can be used any known (meth)acrylic type polymerizable monomers inclusive of those described above.

When the metal oxide ceramics to which the primer of the invention is applied is a dental prosthetic, a dental cement is used as the adhesive material. As the dental cement, there can be used any known resin-reinforced glass ionomer cement, resin ionomer cement or resin cement without limitation. The dental cement contains a (meth)acrylic type polymerizable monomer, a polymerization initiator and a filler. The content of the filler is, usually, 1 to 10,000 parts by mass and, more preferably, 10 to 2,000 parts by mass per 100 parts by mass of the (meth)acrylic type polymerizable monomer. The polymerization initiator is used, usually, in an amount of 0.01 to 20 parts by mass per 100 parts by mass of the (meth)acrylic type polymerizable monomer.

<Primer Kit>

As described already, when the dental cement is to be adhered to the prosthetic of metal oxide ceramics, the primer composition of the invention can be favorably applied onto the surface of adhesion in advance. In this case, it is convenient if the primer composition of the invention is used as an adhesion kit for the prosthetic of metal oxide ceramics in combination with the dental cement.

Further, the primer composition of the present invention contains the acidic group-containing polymerizable monomer and, therefore, exhibits adhering property to some extent to other prosthetics, too. This is because the monomer forms a hydrogen bond with a metal atom in the prosthetic. By effectively adding adhering components to other prosthetics, therefore, the primer composition of the invention can also be used as a primer for other prosthetics, e.g., as a primer for prothetics of a base metal alloy, for prosthetics of a novel metal alloy and for prosthetics of ceramics. In the primer for prosthetics of a novel metal alloy, for example, it has been known that a sulfur atom-containing polymerizable monomer which is a polymerizable monomer serves as an effective adhering component. That is, since the sulfur atom in the monomer forms a chemical bond with a novel metal atom, the primer blended with the sulfur atom-containing polymerizable monomer effectively works as a primer for the prosthetics of the novel metal alloy. By adding the sulfur atom-containing polymerizable monomer of a predetermined amount to the primer composition of the present invention, therefore, the primer composition of the present invention can be transformed into a primer for the prosthetics of the novel metal alloy.

As the above sulfur atom-containing polymerizable monomer, there have been known those disclosed, for example, in JP-A-2000-248201 or, concretely, radically polymerizable compounds represented by the following general formulas (a1) to (a5) that are capable of forming a mercapto group (SH) by tautomerism, radically polymerizable disulfide compounds represented by the following general formulas (a6) to (a9), and radically polymerizable thioether compounds represented by the following general formulas (a10) and (a11).

[Chemical 8]

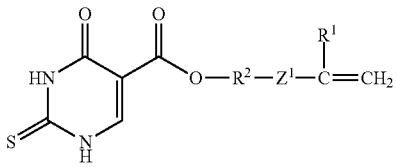
(a1)

[Chemical 9]

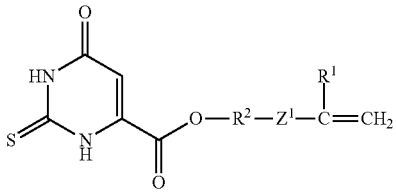
(a2)

[Chemical 10]

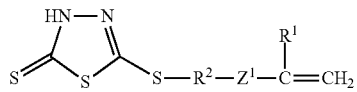
(a3)

[Chemical 11]

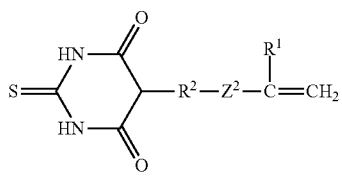
(a4)

[Chemical 12]

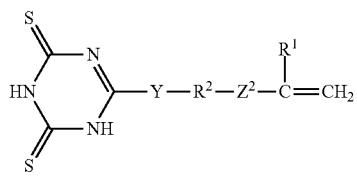
(a5)

[Chemical 13]

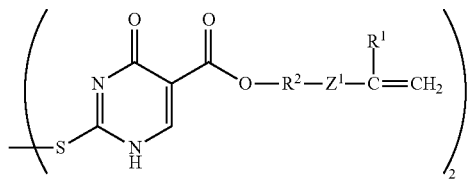
(a6)

[Chemical 14]

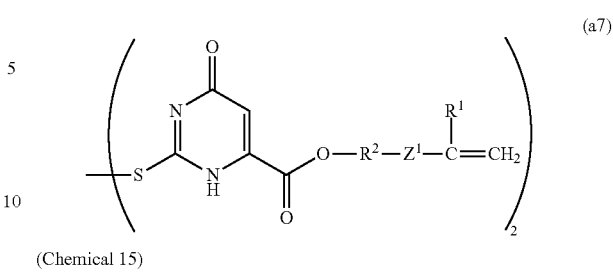
(a7)

[Chemical 15]

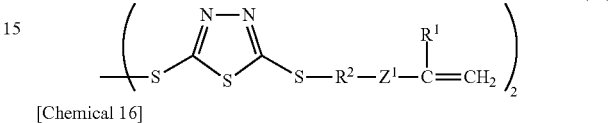
(a8)

[Chemical 16]

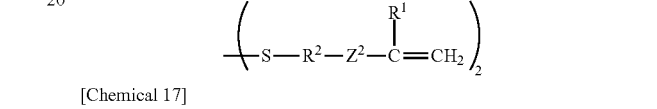
(a9)

[Chemical 17]

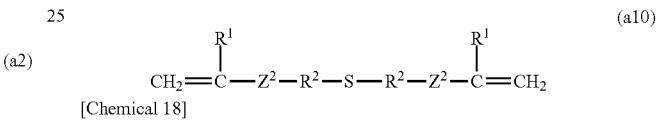
(a10)

[Chemical 18]

(a11)

In the above formulas (a1) to (a11),
$R^1$ is a hydrogen atom or a methyl group,
$R^2$ is an alkylene group having 1 to 12 carbon atoms, a group —$CH_2$—$C_6H_4$—$CH_2$— or a group —$(CH_2)p$-Si$(CH_3)_2$—$(CH_2)q$ (wherein p and q are integers of 1 to 5),
$Z^1$ is a group —O—CO—, a group —$OCH_2$— or a group —$OCH_2$—$C_6H_4$—,
$Z^2$ is a group —O—CO—, a group —$C_6H_4$— or a bonding hand (group $R^2$ and an unsaturated carbon are directly bonded together), and
Y is —S—, —O— or —N(R')— (wherein R' is a hydrogen atom or an alkyl group having 1 to 5 carbon atoms).

Among them, it is desired to use radically polymerizable compounds represented by the above general formulas (a1) to (a5) that are capable of forming a mercapto group (SH) by tautomerism from the standpoint of adhering property.

Further, it has been known that the silane coupling agent is a component effective for the prosthetics of ceramics that contain silica as a chief component. Therefore, the primer composition of the present invention to which the silane coupling agent is added can be preferably used not only for the prosthetics of metal oxide ceramics but also for the dental prosthetics of ceramics that contain silica as a chief component. Concrete examples of the silane coupling agent having a polymerizable group that can be preferably used include γ-methacryloyloxypropyltrimethoxysilane, γ-methacryloyloxypropyltri(trimethyloxy)silane, ω-methacryloyloxydecyltrimethoxysilane and γ-methacryloyloxypropylpentamethyldisoloxane. These coupling agents can be used in one kind or in a combination of two or more kinds.

As will be understood from the above description, the primer composition of the present invention can be used as a primer composition for the prosthetics of metal oxide ceramics. Separately, further, use is made of a composition "as a primer assistant for expanding adaptability" in which an adhesive component such as a sulfur atom-containing polymerizable monomer (hereinafter simply called sulfur type monomer) and silane coupling agent effective for other prosthetics are dissolved or dispersed in an organic solvent. By combining these compositions, there can be obtained an overall primer kit for dental prosthetics that can be used for the prosthetics of other materials, too. That is, in the overall kit, the primer composition of the present invention is used as a primer for the prosthetics of metal oxide ceramics and for the prosthetics of base metal alloys. For the other prosthetics, the primer assistant for expanding adaptability is used in a predetermined amount being added to the primer composition of the present invention while being irradiated with inert light such as red light. As a result, the overall kit can be used as a primer not only for the prosthetics of metal oxide ceramics but also for any other prosthetics.

In the above primer assistant for expanding adaptability, there is no particular limitation on the organic solvent provided it is capable of homogeneously dissolving or dispersing the adhesive component (sulfur type monomer and/or silane coupling agent) and can be homogeneously mixed with the primer composition of the present invention. Usually, however, it is desired to use the same solvent as the organic solvent (C) that is added to the primer composition of the present invention. As required, further, the primer assistant for expanding adaptability may be blended with additives such as polymerization inhibitor and the like.

It is desired that the concentration of the adhesive component in the primer assistant for expanding adaptability is set to be, for example, 0.1 to 20% by mass and, particularly, 0.5 to 15% by mass. If the concentration is too low, the amount of the organic solvent becomes too large when the primer assistant for expanding adaptability is added to the primer composition of the invention, and an extended period of time is required for removing the organic solvent by blowing the air and the workability decreases. Further, if the concentration of the adhesive component is too high, it may become difficult to homogeneously disperse the adhesive component when the primer assistant for expanding adaptability is added to the primer composition of the invention.

As for the adhesive component, further, both the sulfur type monomer and the silane coupling agent may be used being dissolved or dispersed in an organic solvent, or either the sulfur type monomer or the silane coupling agent may be used. When either one is used, it is desired that, for example, the one obtained by mixing the sulfur type monomer into the organic solvent is used as a primer assistant for the noble metal prosthetics and the one obtained by mixing the silane coupling agent to the organic solvent is used as a primer assistant for the prosthetics of ceramics that use silica as a chief component. Concretely, as an overall primer kit, use is made of a package that contains the sulfur type monomer-containing primer assistant for expanding adaptability and a package that contains the silane coupling agent-containing primer assistant for expanding adaptability in combination with a package that contains the primer composition of the present invention.

When the above overall primer kit is used as a primer for other prosthetics (as a primer for the prosthetics of base metal alloys or novel metal alloys) by utilizing the improved adhering property of the sulfur type monomer, it is desired that the concentration of the sulfur type monomer mixed to the primer composition of the invention is 0.01 to 10% by mass per the whole polymerizable monomers. When the above overall primer kit is used as a primer for other prosthetics (e.g., as a primer for the prosthetics of ceramics containing silica as a chief component) by utilizing the improved adhering property of the silane coupling agent, it is desired that the concentration of the silane coupling agent mixed to the primer composition of the invention is 0.1 to 15% by mass per the whole polymerizable monomers.

EXAMPLES

The present invention will now be concretely described by way of Examples and Comparative Examples which, however, are not to limit the invention. Further, it does not mean that the combinations of features described in Examples are all essential for solving the problems of the invention. Abbreviated names, abbreviated signs, method of measuring adhering property and method of measuring the amount of polyvalent metal ions appearing in Examples are as described below.
<(A) Polymerizable Monomers Containing not Less than 5% by Mass of Acidic Group-Containing Polymerizable Monomer>
[(A1) Acidic Group-Containing Polymerizable Monomers]
SPM: A mixture of a 2-methacryloyloxyethyl dihydrogenphosphate and a bis(2-methacryloyloxyethyl)hydrogenphosphate (mole ratio 1:1)
MAC-10: 11-Methacryloyloxy-1,1-undecanedicarboxylic acid
MAC-17: 18-Methacryloyloxy-1,1-octadecanedicarboxylic acid
MDP: 10-Methacryloyloxydecyl dihydrogenphosphate
MHDP: 16-Methacryloyloxyhexadecyl dihydrogenphosphate
[(A2) Polymerizable Monomers without Acidic Group]
UDMA: A mixture of a 1,6-bis(methacrylethyloxycarbonylamino)-2,2,4-trimethylhexane and a 1,6-bis(methacrylethyloxycarbonylamino)-2,4,4-trimethyl hexane
GMA: 2,2-Bis(4-(2-hydroxy-3-methacryloxypropoxy)phenyl) propane 3G: Triethylene glycol dimethacrylate
AAEM: 2-Methacryloxyethylacetyl acetate
<(B) Sources of Polyvalent Metal Ions>
[Polyvalent Metal Compounds]
$Ti(O-nBu)_4$: Titanium tetrabutoxide
$Ti(O-iPr)_4$: Titanium tetraisopropoxide
$TiF_4$: Titanium fluoride
$Zr(O-iPr)_4$: Zirconium tetraisopropoxide
$ZrF_4$: Zirconium fluoride
$W(O-iPr)_4$: Tungsten (IV) tetraisopropoxide
$Al(O-iPr)_3$: Aluminum triisopropoxide
$AlF_3$: Aluminum fluoride
$La(O-iPr)_3$: Lanthanum triisopropoxide
$La(OH)_3$: Lanthanum hydroxide
$Sc(O-iPr)_3$: Scandium triisopropoxide
$Yb(O-iPr)_3$: Ytterbium triisopropoxide
$Mn(acec)_3$: Manganese (III) acetylacetonate
$Fe(O-Et)_3$: Iron (III) ethoxide
$Ca(OH)_2$: Calcium hydroxide
$Mg(OH)_2$: Magnesium hydroxide
<(C) Organic Solvents>
AC: Acetone
EtOH: Ethanol
IPA: Isopropanol
<(D) Polymerization Initiators>
BMOV: Bis(maltolato)oxovanadium (IV)
PhBTEOA: Tetraphenyl borate triethanolamine salt <Other Blending Agents>
[Sulfur Type Monomers]
MTU-6: 6-Methacryloyloxyhexyl-2-thiouracyl-5-carboxylate
[Silane Coupling Agent]
MPS: 3-Methacryloyloxypropyltrimethoxysilane
<Adhering Property to the Prosthetics of Metal Oxide Ceramics>

Zirconia and alumina as metal oxide ceramics were polished with a water-resistant #120 polishing paper. Thereafter, the metal oxide ceramics were subjected to the sand-blast treatment, washed with ultrasonic waves, and were naturally dried. An adhesive tape perforated with a 3 mm φ hole was stuck onto the treated surfaces to fix the junction areas. Pre-treating materials of Examples and Comparative Examples were applied onto the junction surfaces by using a brush. After the solvent was air-dried, round SUS304 rods of 8 mm φ×18 mm that have been polished in advance were adhered to the junction surfaces by using a dental adhesive resin cement (Bistite II manufactured by Tokuyama Dental Co.). All twelve adhesion test pieces were dipped in water of 37° C. for 24 hours. By using an Autograph manufactured by Shimazu Seisakusho Co. (crosshead speed of 2 mm/min.), six test pieces were measured in their state for their tensile adhering strengths and the other remaining six test pieces were measured for their tensile adhering strengths after they were subjected to the thermal cycles (TC) of 3000 times each thermal cycle consisting of dipping the test pieces in cold water of 4° C. and in hot water of 60° C. for one minute, respectively. The measured values of the two groups each consisting of six test pieces were averaged and regarded as the measured results, respectively.

<Method of Measuring the Amount of Polyvalent Metal Ions>

The primer composition of the present invention was prepared and was stirred for 15 hours. Thereafter, the sample primer composition was weighed and put into a 100-ml sample tube, and was diluted into 0.1% by volume with IPA. The solution was measured for its amount of ions (ppm) by the ICP (inductively coupled plasma) emission spectroscopy to calculate a concentration of polyvalent metal ions (mmols/g) contained per gram of the polymerizable monomer component (A). When a plurality of kinds of polyvalent metal ions were present, the concentration of ions of each of the kinds were multiplied by their respective valencies and were added up to calculate the amount of polyvalent metal ions/meq per gram of the polymerizable monomer component (A).

Example 1

(A1) An acidic group-containing polymerizable monomer: 1.0 g of SPM, 4.5 g of MAC-10;
(A2) A polymerizable monomer without acidic group: 4.5 g of UDMA;
(B) A source of polyvalent metal ions: 0.03 g of Ti(O-nBu)$_4$; and
(C) An organic solvent: 23 g of ethanol (EtOH);

were stirred and mixed together to prepare a primer composition of the present invention (one-package type). The primer composition was measured for its concentration of polyvalent metal ions and strength of adhesion to the prosthetics of metal oxide ceramics. The results were as shown in Table 1.

Examples 2 to 20

Primer compositions were prepared in the same manner as in Example 1 but changing the recipe into components shown in Table 1, and were evaluated in the same manner to obtain results as shown in Table 1.

Examples 21 to 41

Primer compositions were prepared in the same manner as in Example 1 but changing the recipe into components shown in Table 2, and were evaluated in the same manner to obtain results as shown in Table 2.

Comparative Examples 1 to 5

Primer compositions were prepared in the same manner as in Example 1 but changing the recipe into components shown in Table 3, and were evaluated in the same manner to obtain results as shown in Table 3.

In Examples 1 to 41, the components were so blended as to satisfy the constitution of the primer compositions of the present invention. In all cases, the primer compositions exhibited excellent initial strengths of adhesion and strengths of adhesion after TC of 3000 times to the metal oxide ceramics.

In Comparative Example 1, on the other hand, the results of adhesion test were those of without the treatment. In Comparative Examples 2 and 3, the components were not so blended as to satisfy the constitution of the primer compositions of the invention. Therefore the strengths of adhesion to the metal oxide ceramics after TC of 3000 times were low in either case. In Comparative Example 4, the strength of adhesion to the metal oxide ceramics was measured by using a silane coupling agent which was a general pre-treating material for the ceramics. However, the strength of adhesion after TC of 3000 times was lower than those of Examples. In Comparative Example 5, the strength of adhesion to the metal oxide ceramics was measured by using the AAEM (patent document 4) which was a pre-treating material for the metal oxide ceramics. Though the initial strength of adhesion was good, the strength of adhesion after TC of 3000 times was lower than those of Examples.

TABLE 1

| | Primer composition (pts. by mass) | | | | Amount of ions per gram of component A/meq |
|---|---|---|---|---|---|
| | Component A | | | | |
| | A1 | A2 | Component B1 | Component C | |
| Ex. 1 | SPM(10), MAC-10(45) | UDMA(45) | Ti(O—nBu)$_4$(0.3) | EtOH(230) | 0.035 |
| Ex. 2 | SPM(55) | ↑ | ↑ | ↑ | ↑ |
| Ex. 3 | MDP(55) | ↑ | ↑ | ↑ | ↑ |
| Ex. 4 | MDP(10), MAC-10(45) | ↑ | ↑ | ↑ | ↑ |
| Ex. 5 | MAC-17(55) | ↑ | ↑ | ↑ | ↑ |
| Ex. 6 | MHDD(55) | ↑ | ↑ | ↑ | ↑ |
| Ex. 7 | MAC-10(55) | ↑ | ↑ | ↑ | ↑ |

TABLE 1-continued

| | | | | | |
|---|---|---|---|---|---|
| Ex. 8 | MAC-10(75) | UDMA(25) | ↑ | ↑ | ↑ |
| Ex. 9 | MAC-10(30) | UDMA(70) | ↑ | ↑ | ↑ |
| Ex. 10 | MAC-10(15) | UDMA(85) | ↑ | ↑ | ↑ |
| Ex. 11 | MAC-10(5) | UMDA(95) | ↑ | ↑ | ↑ |
| Ex. 12 | SPM(10), MAC-10(45) | UDMA(15) | ↑ | ↑ | ↑ |
| Ex. 13 | ↑ | GMA(18), 3G(12) | ↑ | ↑ | ↑ |
| | | GMA(36), 3G(9) | | | |
| Ex. 14 | ↑ | GMA(18), 3G(27) | ↑ | ↑ | ↑ |
| Ex. 15 | ↑ | 3G(45) | ↑ | ↑ | ↑ |
| Ex. 16 | ↑ | UDMA(45) | Ti(O—nBu)$_4$(3) | ↑ | 0.353 |
| Ex. 17 | ↑ | ↑ | Ti(O—nBu)$_4$(6) | ↑ | 0.705 |
| Ex. 18 | ↑ | ↑ | Ti(O—iPr)$_4$(5) | ↑ | 0.704 |
| Ex. 19 | ↑ | ↑ | TiF$_4$(2.2) | ↑ | 0.710 |
| Ex. 20 | ↑ | ↑ | Zr(O—iPr)$_4$(5.8) | ↑ | 0.708 |

| | Adhering strength/MPa (standard deviation) | | | |
|---|---|---|---|---|
| | Zirconia | | Alumnina | |
| | Initially | After 3000 TCs | Initially | After 3000 TCs |
| Ex. 1 | 22.1(2.5) | 15.3(4.8) | 22.1(2.6) | 15.1(4.3) |
| Ex. 2 | 18.9(2.3) | 11.9(5.8) | 18.9(2.4) | 12.0(5.9) |
| Ex. 3 | 25.1(2.5) | 15.9(4.1) | 25.1(2.6) | 15.3(4.4) |
| Ex. 4 | 24.3(2.1) | 15.7(4.7) | 24.3(2.2) | 15.2(4.7) |
| Ex. 5 | 20.6(2.2) | 14.2(5.1) | 20.6(2.3) | 14.3(5.1) |
| Ex. 6 | 20.8(3.1) | 14.2(5.2) | 20.9(3.2) | 14.1(4.9) |
| Ex. 7 | 23.1(2.9) | 15.2(4.1) | 23.1(2.1) | 15.2(4.5) |
| Ex. 8 | 20.1(2.9) | 14.2(4.1) | 20.0(2.1) | 14.2(4.6) |
| Ex. 9 | 23.2(2.8) | 15.6(4.2) | 23.1(2.3) | 15.2(4.4) |
| Ex. 10 | 20.1(2.2) | 14.2(4.8) | 20.0(2.5) | 14.0(4.9) |
| Ex. 11 | 19.1(2.9) | 13.2(4.1) | 19.6(2.1) | 13.6(4.8) |
| Ex. 12 | 22.1(2.4) | 15.2(4.2) | 21.9(2.6) | 15.4(4.7) |
| Ex. 13 | 22.3(2.8) | 15.2(4.0) | 22.1(2.9) | 15.7(4.6) |
| Ex. 14 | 21.5(2.5) | 14.9(4.5) | 21.6(2.6) | 15.0(4.9) |
| Ex. 15 | 20.6(2.5) | 13.9(5.0) | 20.7(2.6) | 13.8(5.1) |
| Ex. 16 | 22.6(2.4) | 15.5(4.5) | 22.6(2.6) | 15.3(4.4) |
| Ex. 17 | 22.5(2.3) | 15.3(4.4) | 22.4(2.4) | 15.5(4.1) |
| Ex. 18 | 22.1(2.5) | 15.5(4.5) | 22.1(2.6) | 15.5(4.6) |
| Ex. 19 | 22.4(2.1) | 15.5(4.4) | 22.4(2.2) | 15.2(4.5) |
| Ex. 20 | 22.5(2.2) | 15.6(4.7) | 22.5(2.3) | 15.5(4.2) |

TABLE 2

| | Primer composition (pts. by mass) | | | | Amount of ions per gram of component A/meq |
|---|---|---|---|---|---|
| | Component A | | | | |
| | A1 | A2 | Component B1 | Component C | |
| Ex. 21 | SPM(10) MAC-10(45) | UDMA (45) | ZrF$_4$(2.9) | EtOH(230) | 0.694 |
| Ex. 22 | ↑ | ↑ | W(O—iPr)$_4$(7.4) | ↑ | 0.704 |
| Ex. 23 | ↑ | ↑ | Al(O—iPr)$_3$(4.8) | ↑ | 0.705 |
| Ex. 24 | ↑ | ↑ | AlF$_3$(2.4) | ↑ | 0.699 |
| Ex. 25 | ↑ | ↑ | La(O—iPr)$_3$(7.5) | ↑ | 0.712 |
| Ex. 26 | ↑ | ↑ | La(OH)$_3$(5) | ↑ | 0.698 |
| Ex. 27 | ↑ | ↑ | Sc(O—iPr)$_3$(5.2) | ↑ | 0.702 |
| Ex. 28 | ↑ | ↑ | Yb(O—iPr)$_3$(8.3) | ↑ | 0.711 |
| Ex. 29 | ↑ | ↑ | Mn(acec)$_3$(6) | ↑ | 0.705 |
| Ex. 30 | ↑ | ↑ | Fe(O—Et)$_3$(4.5) | ↑ | 0.707 |
| Ex. 31 | ↑ | ↑ | Ca(OH)$_2$(2.6) | ↑ | 0.702 |
| Ex. 32 | ↑ | ↑ | Mg(OH)$_2$(2.1) | ↑ | 0.720 |
| Ex. 33 | ↑ | ↑ | Ti(O—nBu)$_4$(6) | EtOH(500) | 0.705 |
| Ex. 34 | ↑ | ↑ | ↑ | EtOH(1000) | ↑ |
| Ex. 35 | ↑ | ↑ | ↑ | EtOH(1300) | ↑ |
| Ex. 36 | ↑ | ↑ | ↑ | EtOH(1600) | ↑ |
| Ex. 37 | ↑ | ↑ | ↑ | EtOH(1900) | ↑ |
| Ex. 38 | ↑ | ↑ | ↑ | EtOH(150) | ↑ |
| Ex. 39 | ↑ | ↑ | ↑ | AC(1000) | ↑ |
| Ex. 40 | ↑ | ↑ | ↑ | AC(1300) | ↑ |
| Ex. 41 | ↑ | ↑ | ↑ | IPA(1000) | ↑ |

TABLE 2-continued

| | Adhering strength/MPa (standard deviation) | | | |
|---|---|---|---|---|
| | Zirconia | | Alumnina | |
| | Initially | After 3000 TCs | Initially | After 3000 TCs |
| Ex. 21 | 22.4(2.3) | 15.2(4.6) | 22.4(2.3) | 15.2(4.1) |
| Ex. 22 | 22.4(2.4) | 15.4(4.1) | 22.4(2.4) | 15.4(4.2) |
| Ex. 23 | 21.8(2.5) | 14.9(4.9) | 21.8(2.6) | 14.7(4.8) |
| Ex. 24 | 21.9(2.4) | 14.8(4.8) | 21.9(2.5) | 14.8(4.9) |
| Ex. 25 | 21.8(2.2) | 14.8(4.9) | 21.8(2.3) | 14.7(4.7) |
| Ex. 26 | 21.7(2.3) | 14.8(4.7) | 21.7(2.4) | 14.9(4.9) |
| Ex. 27 | 21.5(2.2) | 14.9(4.9) | 21.5(2.3) | 14.8(4.7) |
| Ex. 28 | 21.4(2.5) | 14.7(4.9) | 21.4(2.6) | 14.9(4.9) |
| Ex. 29 | 21.6(2.3) | 14.8(4.8) | 21.6(2.4) | 14.8(4.7) |
| Ex. 30 | 21.7(2.5) | 14.9(4.7) | 21.7(2.6) | 14.9(4.9) |
| Ex. 31 | 20.1(2.6) | 13.9(5.1) | 20.1(2.7) | 13.7(5.2) |
| Ex. 32 | 20.2(2.7) | 13.8(5.1) | 20.2(2.8) | 13.9(5.1) |
| Ex. 33 | 23.6(2.5) | 15.5(3.2) | 23.7(2.6) | 15.4(3.3) |
| Ex. 34 | 25.4(2.5) | 16.5(1.5) | 25.3(2.4) | 16.9(1.2) |
| Ex. 35 | 24.9(2.6) | 15.5(2.5) | 24.7(2.7) | 15.4(2.5) |
| Ex. 36 | 20.6(2.5) | 13.7(3.5) | 20.2(2.8) | 13.5(3.7) |
| Ex. 37 | 18.0(2.8) | 11.5(6.5) | 18.1(2.9) | 11.2(6.6) |
| Ex. 38 | 18.3(2.9) | 11.4(6.7) | 18.2(2.8) | 11.3(6.8) |
| Ex. 39 | 24.7(2.5) | 16.6(1.1) | 24.6(2.6) | 16.7(1.1) |
| Ex. 40 | 24.6(2.3) | 15.5(2.5) | 24.8(2.4) | 15.3(2.7) |
| Ex. 41 | 25.6(2.5) | 16.4(1.3) | 25.2(2.5) | 16.6(1.1) |

TABLE 3

| | Primer composition (pts. by mass) | | | | | Amount of ions per gram of component A/meq |
|---|---|---|---|---|---|---|
| | Component A | | | | | |
| | A1 | A2 | Component B1 | Component C | Others | |
| Comp. Ex. 1 | Untreated | Untreated | Untreated | Untreated | Untreated | Untreated |
| Comp. Ex. 2 | SPM(10) MAC-10(45) | UDMA (45) | — | EtOH (230) | — | — |
| Comp. Ex. 3 | — | UDMA (100) | Ti—(O-nBu)$_4$ (6) | ↑ | — | 0.705 |
| Comp. Ex. 4 | SPM(10) MAC-10(45) | UDMA (45) | — | ↑ | MPS (2) | — |
| Comp. Ex. 5 | — | AAEM (100) | — | AC (900) | — | — |

| | Adhering strength/MPa (standard deviation) | | | |
|---|---|---|---|---|
| | Zirconia | | Alumnina | |
| | Initially | After 3000 TCs | Initially | After 3000 TCs |
| Comp. Ex. 1 | 13.0(3.1) | 4.2(2.1) | 13.1(2.9) | 4.1(2.1) |
| Comp. Ex. 2 | 15.6(2.7) | 5.1(2.2) | 15.9(2.1) | 5.1(3.2) |
| Comp. Ex. 3 | 13.1(1.1) | 5.1(2.3) | 13.0(2.1) | 5.5(2.3) |
| Comp. Ex. 4 | 16.7(3.5) | 5.8(3.3) | 16.2(3.5) | 6.2(3.5) |
| Comp. Ex. 5 | 20.1(3.1) | 6.2(3.8) | 22.1(4.5) | 6.7(3.3) |

Example 42

Recipe 1 (Primer I)

(A1) An acidic group-containing polymerizable monomer: 1.0 g of SPM, 4.5 g of MAC-10;

(A2) A polymerizable monomer without acidic group: 1.5 g of UDMA, 1.8 g of GMA and 1.2 g of 3G; and (C) An organic solvent: 100 g of ethanol (EtOH).

Recipe 2 (Primer II)

(B) A source of polyvalent metal ions: 0.6 g of Ti(O-nBu)$_4$; and (C) An organic solvent: 100 g of ethanol (EtOH).

The above components of the above recipes were stirred and mixed together to prepare a primer composition of the present invention (two-package type). Just before the use, the above two liquids were picked up in equal amounts and were mixed together to obtain a homogeneous solution thereof. The thus obtained primer composition was measured for its concentration of polyvalent metal ions and strength of adhesion to the prosthetics of metal oxide ceramics. The results were as shown in Table 4.

Examples 43 to 45, Comparative Examples 6 to 9

Primer compositions were prepared in the same manner as in Example 42 but changing the recipes into components shown in Table 4, and were evaluated in the same manner to obtain results as shown in Table 4.

In Examples 42 to 45, the components were so blended as to satisfy the constitution of the primer compositions of the present invention. In all cases, the primer compositions exhibited excellent initial strengths of adhesion and strengths of adhesion after TC of 3000 times to the metal oxide ceramics. In Comparative Examples 6 to 9, on the other hand, the components were not so blended as to satisfy the constitution of the primer compositions of the invention. Therefore, the strengths of adhesion to the metal oxide ceramics after TC of 3000 times were low in all cases.

(B) A source of polyvalent metal ions: 0.006 g of $Ti(O-nBu)_4$; and
(C) An organic solvent: 23 g of ethanol (EtOH);

were stirred and mixed together to prepare a primer composition of the present invention (one-package type). The primer composition was measured for its concentration of polyvalent metal ions and strength of adhesion to the prosthetics of metal oxide ceramics. The results were as shown in Table 5.

Examples 47 to 51, Comparative Examples 10 and 11

Primer compositions were prepared in the same manner as in Example 46 but changing the recipes into components shown in Table 5, and were evaluated in the same manner to obtain results as shown in Table 5.

In Examples 46 to 51, the components were so blended as to satisfy the constitution of the primer compositions of the present invention. In all cases, the primer compositions exhibited excellent initial strengths of adhesion and strengths

TABLE 4

| | Primer I composition (pts. by mass) | | | | Primer II composition (pts. by mass) | | | Amount of ions per gram of component |
|---|---|---|---|---|---|---|---|---|
| | Component A | | Component | Component | Component | Component | Component | |
| | A1 | A2 | C | D | B1 | C | D | A/meq |
| Ex. 42 | SPM(10) MAC-10 (45) | UDMA(15) GMA(18) 3G(12) | EtOH (1000) | — | $Ti(O-nBu)_4$ (6) | EtOH (1000) | — | 0.705 |
| Ex. 43 | ↑ | ↑ | ↑ | BMOV (0.15) | ↑ | ↑ | — | ↑ |
| Ex. 44 | ↑ | ↑ | ↑ | — | ↑ | ↑ | PhBTEOA (2.5) | ↑ |
| Ex. 45 | ↑ | ↑ | ↑ | BMOV (0.15) | ↑ | ↑ | ↑ | ↑ |
| Comp. Ex. 6 | ↑ | ↑ | ↑ | — | — | ↑ | — | — |
| Comp. Ex. 7 | ↑ | ↑ | ↑ | BMOV (0.15) | — | ↑ | PhBTEOA (2.5) | — |
| Comp. Ex. 8 | — | ↑ | ↑ | — | $Ti(O-nBu)_4$ (6) | ↑ | — | 0.705 |
| Comp. Ex. 9 | — | ↑ | ↑ | BMOV (0.15) | ↑ | ↑ | PhBTEOA (2.5) | ↑ |

| | Adhering strength/MPa (standard deviation) | | | |
|---|---|---|---|---|
| | Zirconia | | Alumnina | |
| | Initially | Durability of 3000 times | Initially | Durability of 3000 times |
| Ex. 42 | 24.4(2.6) | 16.7(1.3) | 24.4(2.6) | 16.5(1.2) |
| Ex. 43 | 25.0(2.0) | 17.7(1.0) | 25.2(2.1) | 17.6(1.1) |
| Ex. 44 | 25.1(2.0) | 17.8(1.1) | 25.3(2.6) | 17.7(1.0) |
| Ex. 45 | 26.3(1.8) | 18.8(0.9) | 26.4(1.9) | 18.9(0.8) |
| Comp. Ex. 6 | 15.8(2.5) | 5.1(2.1) | 15.9(2.1) | 5.1(3.1) |
| Comp. Ex. 7 | 16.6(2.3) | 6.1(2.0) | 16.1(2.0) | 6.9(3.0) |
| Comp. Ex. 8 | 12.1(2.1) | 5.1(2.3) | 12.9(2.5) | 5.6(2.3) |
| Comp. Ex. 9 | 13.1(2.0) | 5.8(2.0) | 13.0(1.2) | 6.1(2.1) |

Example 46

(A1) An acidic group-containing polymerizable monomer: 1.0 g of SPM, 4.5 g of MAC-10;
(A2) A polymerizable monomer without acidic group: 4.5 g of UDMA;

of adhesion after TC of 3000 times to the metal oxide ceramics. In Comparative Examples 10 and 11, on the other hand, the results were those of the primer compositions containing water. Therefore the initial strengths of adhesion and strengths of adhesion to the metal oxide ceramics after TC of 3000 times were low in all cases.

TABLE 5

| | Primer composition (pts. by mass) | | | | | Amount of ions per gram of component A/meq |
|---|---|---|---|---|---|---|
| | Component A | | | | | |
| | A1 | A2 | Component B1 | Component C | Others | |
| Ex. 46 | SPM(10) MAC-10(45) | UDMA(45) | Ti(O-nBu)$_4$(0.06) | EtOH (230) | — | 0.007 |
| Ex. 47 | ↑ | ↑ | Ti(O-nBu)$_4$(3) | ↑ | — | 0.352 |
| Ex. 48 | ↑ | ↑ | Ti(O-nBu)$_4$(6) Zr(O-iPr)$_4$(5.8) | ↑ | — | 1.41 |
| Ex. 49 | ↑ | ↑ | Ti(O-nBu)$_4$(24) | ↑ | — | 2.82 |
| Ex. 50 | ↑ | ↑ | Ti(O-nBu)$_4$(18) Zr(O-iPr)$_4$(17.4) | ↑ | — | 4.23 |
| Ex. 51 | ↑ | ↑ | Ti(O-nBu)$_4$(48) | ↑ | — | 5.63 |
| Comp. Ex. 10 | ↑ | ↑ | Ti(O-nBu)$_4$(3) | ↑ | water(0.5) | 0.352 |
| Comp. Ex. 11 | ↑ | ↑ | Ti(O-nBu)$_4$(6) | ↑ | water(2) | 0.705 |

| | Adhering strength/MPa(standard deviation) | | | |
|---|---|---|---|---|
| | Zirconia | | Alumnina | |
| | Initially | After 3000 TCs | Initially | After 3000 TCs |
| Ex. 46 | 18.2(2.7) | 12.1(4.1) | 17.9(3.1) | 12.8(3.9) |
| Ex. 47 | 21.2(3.2) | 14.1(4.3) | 20.9(2.6) | 14.0(3.6) |
| Ex. 48 | 23.5(2.9) | 15.8(4.1) | 23.4(2.3) | 15.7(4.1) |
| Ex. 49 | 21.5(2.4) | 14.5(4.1) | 21.8(2.2) | 14.2(4.0) |
| Ex. 50 | 19.8(2.0) | 13.5(4.7) | 20.5(2.4) | 13.7(3.1) |
| Ex. 51 | 19.5(3.8) | 13.2(4.0) | 19.1(2.5) | 13.0(2.8) |
| Comp. Ex. 10 | 16.2(3.4) | 6.2(2.0) | 15.1(2.0) | 7.1(2.9) |
| Comp. Ex. 11 | 15.8(3.0) | 7.2(2.1) | 15.1(2.3) | 7.6(2.1) |

The invention claimed is:

1. A primer composition for metal oxide ceramics, comprising:
   (A) a polymerizable monomer containing 30 to 70% by mass of an acidic group-containing polymerizable monomer;
   (B) polyvalent metal ions; and
   (C) an organic solvent;
   wherein a content of water is not more than 0.1 parts by weight per 100 parts by weight of the primer composition.

2. The primer composition for metal oxide ceramics according to claim 1, wherein the content of the polyvalent metal ions (B) is 0.001 to 6.00 meq per gram of said polymerizable monomer component (A).

3. The primer composition for metal oxide ceramics according to claim 1, wherein the organic solvent (C) is contained in an amount of 200 to 1750 parts by mass per 100 parts by mass of said polymerizable monomer component (A).

4. The primer composition for metal oxide ceramics according to claim 1, wherein the polyvalent metal ions (B) are metal ions resulting from a polyvalent metal compound.

5. The primer composition for metal oxide ceramics according to claim 1, wherein a polymerization initiator (D) is, further, contained.

6. A dental primer composition comprising the primer composition for metal oxide ceramics of claim 1.

7. A dental adhesion kit for prosthetics of metal oxide ceramics, comprising the dental primer composition of claim 6 and a dental cement.

8. A method of treating surfaces of prosthetics by applying the dental primer composition of claim 6 onto a surface of a dental prosthetic of metal oxide ceramics and, thereafter, removing the organic solvent by blowing air.

* * * * *